United States Patent
Wegner et al.

(10) Patent No.: US 6,603,045 B2
(45) Date of Patent: Aug. 5, 2003

(54) PREPARATION OF PHOSPHONIUM SALTS

(75) Inventors: Christoph Wegner, Schifferstadt (DE); Joachim Paust, Neuhofen (DE); Michael John, Lambsheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/103,770

(22) Filed: Mar. 25, 2002

(65) Prior Publication Data

US 2002/0128516 A1 Sep. 12, 2002

Related U.S. Application Data

(63) Continuation of application No. 09/693,823, filed on Oct. 23, 2000, now Pat. No. 6,433,226, which is a continuation of application No. 09/130,521, filed on Aug. 7, 1998, now Pat. No. 6,187,959.

(30) Foreign Application Priority Data

Aug. 8, 1997 (DE) ......................... 197 34 446

(51) Int. Cl.$^7$ .................................................. C07F 9/54
(52) U.S. Cl. ........................................... 568/9; 585/508
(58) Field of Search ............................. 568/9; 585/508, 585/600, 310, 506, 507

(56) References Cited

U.S. PATENT DOCUMENTS

| 4,182,731 A | 1/1980 | Schulz et al. |
| 4,595,783 A | 6/1986 | Vogel et al. |
| 5,166,445 A | 11/1992 | Meyer |

*Primary Examiner*—Jean F. Vollano
(74) *Attorney, Agent, or Firm*—Oblon, Spivak, McClelland, Maier & Neustadt, P.C.

(57) ABSTRACT

Phosphonium salts are prepared by reacting an alkanol with triarylphosphine and sulfonic acids in a solvent.

22 Claims, No Drawings

PREPARATION OF PHOSPHONIUM SALTS

This application is a Continuation of U.S. application Ser. No. 09/693,823, filed Oct. 23, 2000, now U.S. Pat. No. 6,433,226 which is a Continuation of U.S. application Ser. No. 09/130,521, filed Aug. 7, 1998, now U.S. Pat. No. 6,187,959.

The present invention relates to a process for preparing 3,7,11-trimethyldodeca-2,4,6, 10-tetraen-1-ylphosphonium salts, to the corresponding phosphonium salts, and to a process for preparing lycopene.

As a rule, the $C_{15}$-phosphonium salts for synthesizing carotenoids are prepared from vinylcarbinols by reaction with triphenylphosphine and a strong acid such as HCl or $H_2SO_4$ in protic solvents (see, for example, J. Chem. Soc., 1965, 2019–2026). Unlike vinyl-β-ionol, which is a precursor used for synthesizing vitamin A and β-carotene, it is possible to react vinylpseudoionol as precursor for preparing lycopene under these standard conditions only with poor yields and with low E/Z selectivities to give the corresponding $C_{15}$-phosphonium salts.

EP 382 067 describes a process in which $C_{15}$-phosphonium salts of lower alkanoic acids are prepared as intermediates because the salts which are mentioned of strong acids always give poor E/Z selectivities and, in the subsequent preparation of lycopene, low yields (byproducts). The salts of the alkanoic acids must be converted back into the chlorides (anion exchange) in an elaborate procedure before the subsequent Wittig reaction. In addition, to obtain a high E/Z ratio in the lycopene, it is necessary to remove (Z) contributions to the phosphonium salt by crystallization.

DE-B 27 29 974 discloses a process for preparing aqueous solutions of polyenyltriarylphosphonium salts of strong acids in acetic acid (see Example 3), although no 3,7,11-trimethyldodeca-2,4,6,10-tetraen-1-ylphosphonium salts, nor any alkanesulfonic acid, are mentioned in the Examples.

It is an object of the present invention to provide a process for preparing phosphonium salts, which in one step results in 3,7,11-trimethyldodeca-2,4,6,10-tetraen-1-ylphosphonium salts which have a high E content and which give high E/Z selectivities on further reaction to lycopene.

We have found that this object is achieved by a process for preparing phosphonium salts of the formula I

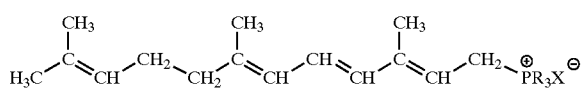

where

R is aryl and $X^{\ominus}$ is $C_nH_{2n+1}$—$SO_3^{\ominus}$ with n=1–4,
Ar—$SO_3^{\ominus}$ with Ar=phenyl, tolyl or
$CF_3$—$CO_3^{\ominus}$, which comprises reacting an alcohol of the formula II

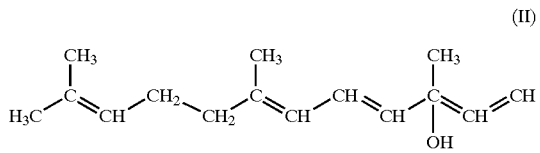

with triarylphosphine and sulfonic acids of the formulae $C_nH_{2n+1}$—$SO_3H$, Ar—$SO_3H$ or $CF_3$—$SO_3H$, where n and Ar have the abovementioned meanings, in a solvent.

This usually entails adding the alcohol to the sulfonic acid in the solvent.

The sulfonic acids which are preferably used are alkanesulfonic acids, eg. ethane- or methanesulfonic acid, especially the industrially available methanesulfonic acid (70%). The reaction is preferably carried out in an alkanecarboxylic acid as solvent, particularly suitable alkanecarboxylic acids having 1–8 carbon atoms, especially acetic acid and propionic acid.

The invention also relates to phosphonium salts of the formula I

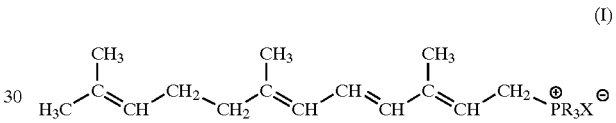

where R is aryl and $X^{\ominus}$ is $C_nH_{2n+1}$—$SO_3^{\ominus}$ with n=1–4, or $CF_3$—$SO_3^{\ominus}$, in particular $CH_3$—$SO_3^{\ominus}$. The term "aryl" means aryl radicals usually occurring in phosphines, such as phenyl, tolyl, naphthyl, each unsubstituted or substituted, especially phenyl.

The invention furthermore relates to a process for preparing lycopene, which comprises reacting a phosphonium salt of the formula I having the meanings for R, X, Ar and n stated in claim 1 with 2,7-dimethyl-2,4,6-octatrienedial.

It is possible by the process according to the invention to convert vinylpseudoionol of the formula II with, for example, methanesulfonic acid in glacial acetic acid into the corresponding phosphonium methanesulfonate in yields of 85–90% and with an E/Z selectivity of 3.7:1. The salt obtained in this way is immediately suitable for Wittig-reaction with 2,7-dimethyl-2,4,6-octatrienedial to prepare lycopene, it being possible to dispense with additional steps such as anion exchange or enrichment of the E component by additional crystallization.

It was surprising that these advantageous results can be obtained with strong acids like the sulfonic acids, since it is stated in EP 382 067 A1 that the preparation of lycopene from salts of strong acids, mentioning halides, sulfates or phosphates, gives only low yields, with formation of unreactive byproducts especially in the preparation of the phosphonium salts (see page 2, lines 5–9). In the process according to the invention it is usual to add vinylpseudoionol (alcohol of the formula II) dropwise to the sulfonic acid, resulting in a high E/Z selectivity.

The process according to the invention is carried out in particular at from 20 to 120° C., preferably at 60 to 100° C., in a conventional way.

The alcohol of the formula II (3,7,11-trimethyldodeca-1,4,6,10-tetraen-3-ol) is also referred to as vinyl-ψ-ionol or vinylpseudoionol and is disclosed, for example, in J. Chem.

Soc. 1965, 2023 or EP 382 067. It can be obtained by known methods from pseudoionone.

The phosphonium salt of the formula I is preferably in the all-E form.

The lycopene prepared by the process according to the invention is used in a conventional way as coloring agent for human or animal foods, as antioxidant or as nutraceutical.

EXAMPLE 1

A mixture of 41.9 g of triphenylphosphine, 13.7 g of methanesulfonic acid (70% strength) and 100 ml of acetic acid was heated to 80° C. and then, over the course of 10 minutes, 24.2 g of 3,7,11-trimethyldodeca-1,4E,6E,10-tetraen-3-ol (91% pure) were added. The mixture was then stirred for 30 minutes before distilling off the acetic acid under 50 mbar. The residue, consisting of 3,7,11-trimethyldodeca-2,4,6,10-tetraen-1-yltriphenyliphosphonium methanesulfonate, was taken up in 100 ml of toluene, which was then likewise distilled off under 50 mbar, to remove the last residues of acetic acid. This procedure was then repeated once more. The residue was taken up in 25 ml of methanol and extracted once with 100 ml, and four times with 50 ml each time, of heptane. The methanolic solution containing the required product was investigated by HPLC with an internal standard. Analysis revealed 50.7 g (90.4%) of 3,7,11-trimethyldodeca-2,4,6,10-tetraen-1-yltriphenylphosphonium methanesulfonate consisting of 39.8 g (71.0%) of all-E isomer, 5.69 g (10.1%) of 6Z isomer and 5.22 g (9.3%) of 2Z isomer. The ratio of the E isomer to the Z isomers is accordingly 3.71.

EXAMPLE 2

A mixture of 39.3 g of triphenylphosphine, 15.1 g of trifluoromethanesulfonic acid and 100 ml of acetic acid was heated to 80° C. and then, over the course of 10 minutes, 23.2 g of (95% pure) 3,7,11-trimethyldodeca-1,4E,6E,10-tetraen-3-ol were added. The mixture was then stirred for 30 minutes before the reaction solution was analyzed by HPLC with an internal standard for content and selectivity. The solution contained 56.7 g (92.2%) of 3,7,11-trimethyldodeca-2,4,6,10-tetraen-1-triphenylphosphonium trifluoromethanesulfonate consisting of 43.7 g (71.1%) of all-E isomer, 6.33 g (10.3%) of 6Z isomer and 6.64 g (0O.8%) of 2Z isomer. The E isomer/Z isomers ratio is accordingly 3.4:1.

EXAMPLE 3

A mixture of 39.3 g of triphenylphosphine, 19.0 g of p-toluenesulfonic acid and 100 ml of acetic acid was heated to 80° C. and then, over the course of 10 minutes, 23.2 g of (95% pure) 3,7,11-trimethyldodeca-1,4E,6E,10-tetraen-3-ol were added. The mixture was then stirred for 30 minutes before the reaction solution was analyzed by HPLC with an internal standard for content and selectivity. The solution contained 53.5 g (84.0%) of 3,7,11-trimethyldodeca-2,4,6,10-tetraen-1-yl-triphenylphosphonium p-toluenesulfonate consisting of 41.5 g (65.2%) of all-E isomer, 6.39 g (10.0%) of 6Z isomer and 5.59 g (8.8%) of 2Z isomer. The E isomer/Z isomers ratio is accordingly 3.5:1.

EXAMPLE 4

A mixture of 41.9 g of triphenylphosphine, 11.0 g of ethanesulfonic acid and 100 ml of acetic acid was heated to 80° C. and then, over the course of 10 minutes, 24.5 g of (90% pure) 3,7,11-trimethyldodeca-1,4E,6E,10-tetraen-3-ol were added. The mixture was then stirred for 30 minutes before the reaction solution was analyzed by HPLC with an internal standard for content and selectivity. The solution contained 49.2 g (85.6%) of 3,7,11-trimethyldodeca-2,4,6,10-tetraen-1-yl-triphenylphosphonium ethanesulfonate consisting of 38.8 g (67.5%) of all-E isomer, 5.62 g (9.8%) of 6Z isomer and 4.76 g (8.3%) of 2Z isomer. The E isomer/Z isomers ratio is accordingly 3.7:1.

EXAMPLE 5

A mixture of 41.9 g of triphenylphosphine, 13.9 g of methanesulfonic acid (69.2% pure) and 100 ml of propionic acid was heated to 8000 and then, over the course of 10 minutes, 24.5 g of (90% pure) 3,7,11-trimethyldodeca-1,4E,6E,10-tetraen-3-ol were added. The mixture was then stirred for 30 minutes before the reaction solution was analyzed by HPLC with an internal standard for content and selectivity. The solution contained 49.9 g (89.0%) of 3,7,11-trimethyldodeca-2,4,6,10-tetraen-1-yl-triphenylphosphonium methanesulfonate consisting of 39.5 g (70.4%) of all-E isomer, 5.81 g (10.3%) of 6Z isomer and 4.60 g (8.2%) of 2Z isomer. The E isomer/Z isomers ratio is accordingly 3.8:1.

COMPARATIVE EXAMPLE

Example 1 of EP 372 067 was reproduced several times as stated in the publication. Before enrichment of the E isomer, the C 15-phosphonium salt was obtained in a yield of 70 to 80% with an E/Z ratio of 2.4–2.6:1.

We claim:

1. A process for preparing a phosphonium salt represented by formula I:

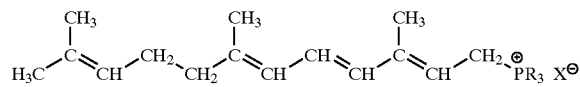

wherein

R is aryl, and $X^{\ominus}$ is Ar—$SO_3^{\ominus}$, wherein Ar is phenyl or tolyl, which comprises reacting an alcohol represented by formula II:

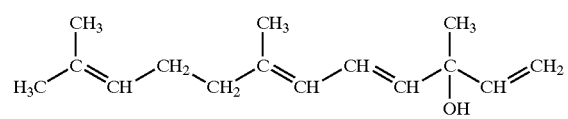

with a triarylphosphine in the presence of a sulfonic acid represented by the formula Ar—$SO_3H$, wherein Ar is as defined above, in a solvent.

2. The process of claim 1, wherein Ar is phenyl.

3. The process of claim 1, wherein Ar is tolyl.

4. The process of claim 1, wherein the solvent is an alkanecarboxylic acid.

5. The process of claim 1, wherein the solvent is an alkanecarboxylic acid having 1–8 carbon atoms.

6. The process of claim 1, wherein the solvent is acetic acid or propionic acid.

7. The process of claim 1, wherein R is phenyl.

8. A process for preparing lycopene, comprising:
(a) reacting an alcohol represented by formula II:

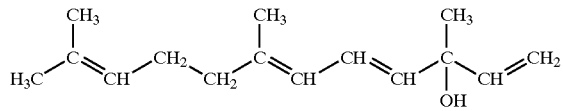

with a triarylphosphine and a sulfonic acid represented by the formula Ar—SO$_3$H, wherein Ar is phenyl or tolyl, to produce a phosphonium salt represented by formula I:

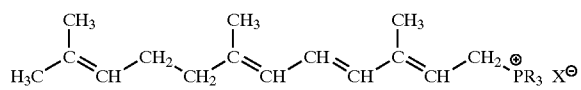

wherein
R is aryl, and
X$^\ominus$ is Ar—SO$_3^\ominus$, wherein Ar is as defined above; and
(b) reacting the phosphonium salt represented by formula I with 2,7-dimethyl-2,4,6-octatriendial, to produce lycopene.

9. The process as claimed in claim 8, wherein Ar is phenyl.

10. The process as claimed in claim 8, wherein Ar is tolyl.

11. The process as claimed in claim 8, wherein (a) is conducted in a solvent.

12. The process as claimed in claim 11, wherein the solvent is an alkanecarboxylic acid.

13. The process as claimed in claim 11, wherein the solvent is an alkanecarboxylic acid having 1–8 carbon atoms.

14. The process as claimed in claim 11, wherein the solvent is acetic acid or propionic acid.

15. The process as claim 8, wherein R is phenyl.

16. A process for preparing a phosphonium salt represented by formula I:

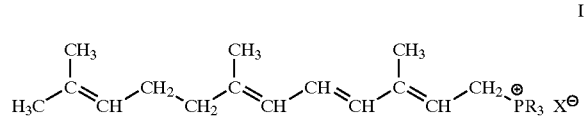

wherein
R is aryl, and
X$^\ominus$ is Ar—SO$_3^\ominus$, wherein Ar is phenyl or tolyl, which consists essentially of reacting an alcohol represented by formula II:

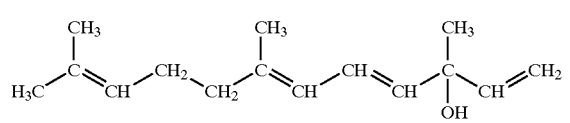

with a triarylphosphine and a sulfonic acid represented by formula Ar—SO$_3$H, wherein Ar is as defined above, in a solvent.

17. The process of claim 16, wherein Ar is phenyl.

18. The process of claim 16, wherein Ar is tolyl.

19. The process of claim 16, wherein the solvent is an alkanecarboxylic acid.

20. The process of claim 16, wherein the solvent is an alkanecarboxylic acid having 1–8 carbon atoms.

21. The process of claim 16, wherein the solvent is acetic acid or propionic acid.

22. The process of claim 16, wherein R is phenyl.

* * * * *